United States Patent [19]

Eiland

[11] Patent Number: Plant 6,178

[45] Date of Patent: May 17, 1988

[54] MAGNOLIA HYBRID CV. MONLAND

[75] Inventor: Robert Eiland, Millbrook, Ala.

[73] Assignee: Monrovia Nursery Company, Azusa, Calif.

[21] Appl. No.: 770,860

[22] Filed: Aug. 29, 1985

[51] Int. Cl.[4] ..... A01H 5/00

[52] U.S. Cl. ..... Plt./51

[58] Field of Search ..... Plt./51

[56] References Cited

U.S. PATENT DOCUMENTS

P.P. 2,617 4/1966 Van Rensselaer ..... Plt. 51

P.P. 5,520 7/1985 Bracken ..... Plt. 51

OTHER PUBLICATIONS

McDaniel J. C. "Variations in Sweet Bay Magnolias" *Morris Arboretum Bulletin,* vol. 17, No. 1, Mar. 1966, pp. 24–29.

*Primary Examiner*—James R. Feyrer

[57] ABSTRACT

A new and distinct selection of *Magnolia grandiflora* hybrid (popularly known as a Magnolia) which hereinafter shall be referred to as *Magnolia grandiflora* cultivar Monland. Due to the characteristics noted in this specification, the selection is believed to be an intraspecific hybrid of *Magnolia grandiflora* and *Magnolia virginiana. Magnolia grandiflora* cultivar. Monland differs from other evergreen Magnolias by possessing a combination of continuously heavy blooming due to a unique blooming pattern, longer foliage which forms a dense crown, a growth habit which is wide spreading and few to no fruit cones produced.

2 Drawing Sheets

BACKGROUND OF THE NEW PLANT

This invention relates to a new and distinct selection of *Magnolia grandiflora* hybrid, a member of the Magnolia family, Magnoliaceae.

My new selection is believed to be an intraspecific hybrid of *Magnolia grandiflora* and *Magnolia virginiana.* In accordance with an article written by Joseph C. McDaniel, *Variations in Sweet Bay Magnolias,* Morris Arboretum Bulletin, March, 1966, Vol. 17, No. 1, it is noted because of overlapping regions of the native habitats of both *Magnolia grandiflora* and *Magnolia virginiana* early natural hybrids are likely to have resulted. With 'Monland' hybridity is believed indicated because of the tree's precocious, profuse and remontant to continuous blooming habit and its lack of seed formation. Only few, mishaped cones are formed and such cones bear few, if any, seeds. The seeds produced are distorted to normal in shape and are apparently nonviable. No seeds have germinated after several attempts to germinate the few seeds formed in successive years.

*Magnolia grandiflora* hybrid cultivar Monland was discovered by me at a local residence in the late sixties, its parentage unknown. After observing heavy blooming in the spring through fall of each year and the unusual and outstanding attributes mentioned in this specification, I felt this tree was worthy of further observation. In October, 1969, I took cuttings and the following year produced seven plants. The original tree at the nearby residence has since been destroyed but the plant that I propagated in 1969 is now sixteen years old and exists in Charmwood Nursery.

The plant to date is known to exist only within the boundaries of Monrovia Nursery, 18331 E. Foothill Boulevard, Azusa, Calif. and Charmwood Nursery, 3740 Charmwood Drive, Millbrook, Ala. This selection has not been offered for sale or described in any publication.

This new selection has been strictly asexually reproduced by grafts at Monrovia Nursery and Charmwood Nursery in order to retain the characteristics of continuously heavy blooming due to a unique blooming pattern, longer foliage which forms a dense crown, a growth habit which is wide spreading and few to no fruit cones produced. Sexual reproduction, to date, has been precluded by the failure of 'Monland' to produce viable seeds. Only a few seeds from this selection have been produced but germination was unsuccessful probably due to hybrid sterility.

SUMMARY OF INVENTION

*Magnolia grandiflora* cv. Monland differs from other evergreen Magnolias by possessing a combination of the following characteristics:

(1) The continuous and heavy blooming period on the Magnolia starts in early May and continues until September or first frost in Alabama. It is believed in a frost-free area this Magnolia shall bloom continuously throughout the year. The blooming pattern is unique on the new selection and is why this Magnolia is in continuous bloom. Generally an evergreen Magnolia shall bloom in summer on the terminal ends of a branch, then vegetative growth shall resume and the following year this new growth shall produce flowers. The new selection will bloom in May, vegetative growth will resume and produce flower buds in summer and flower again that same year. This unique blooming pattern of series of flushes on new wood results in a continuously year around (in mild climates) flower display.

(2) The foliage on my new selection is longer and wider on the average when compared to previous Magnolias that have been described and patented. My selection has a leaf blade length ranging: 6–9¾ inches
width ranging: 2½–4½ inches
U.S. Plant Pat. No. 2,617
length ranging: 4¾–6¾ inches
width ranging: 2–2¾ inch
U.S. Plant Pat. No.: 5,520
length ranging: 4–7½ inches
width ranging: 2–3 inches Foliage on my new selection forms an extremely dense crown on trees 7 to 8 years and older. The foliage cover is so dense the trunk and branches are not visible. Even though this dense foliage cover shades the inside of the tree, if branches are pulled back blooms are even present within this dense shade.

(3) The new selection has a wide spreading habit. This growth shape is unusual as *Magnolia grandifloras* have a tendency to have an upright pyramidal growth habit.

(4) The production of fruiting cones on my new selection is minimal ranging from none some years to the maximum number of four I have found on a sixteen year old tree. Though this selection produces an unusual abundance of flowers the fruiting cones are rare to find. These cones are small, irregularly distorted in shape and generally contain 1 to 2 seeds. The maximum number found in a cone was 12 seeds. The few seeds found the past 3 years have never germinated. These unusual distorted and small number of cones produced after heavy blooming is likely due to irregular fertilization or abortion of the ovules which certainly suggests the selection may possess hybrid sterility.

BRIEF DESCRIPTION OF THE DRAWINGS

Two of the photos exhibit stages of anthesis.

BOTANICAL DESCRIPTION

Figure 1:
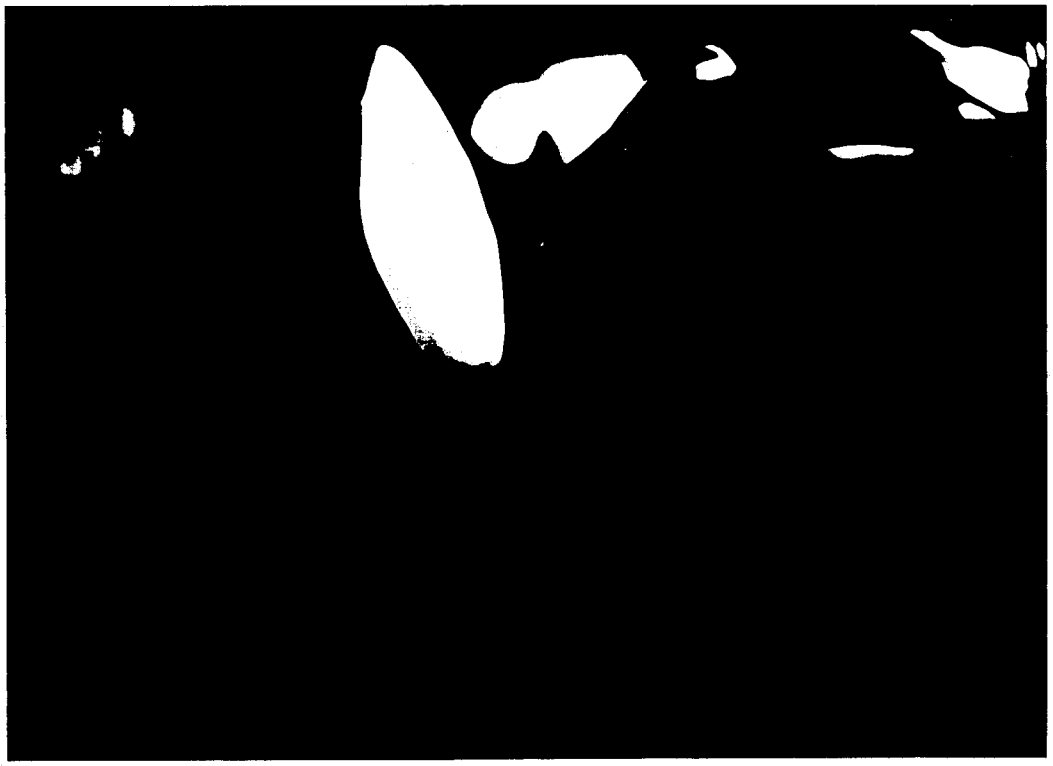
FIG. 1 displays the size and shape of the flower bud and the lustrous foliage.
Figure 2:
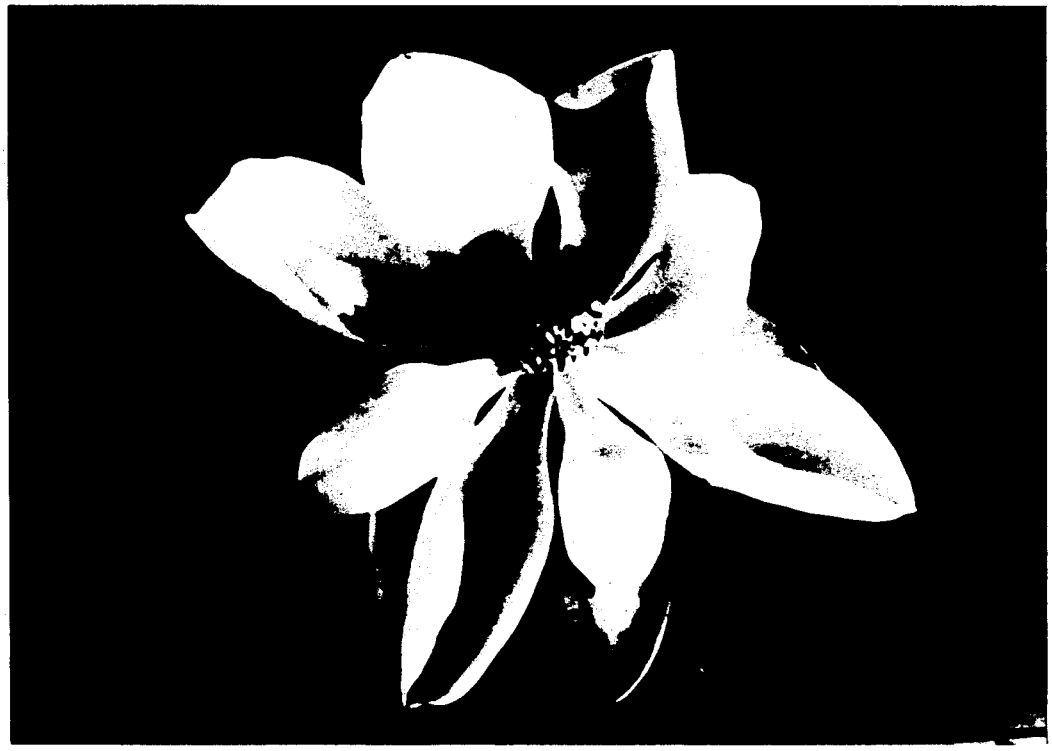
FIG. 2 exhibits a large creamy white flower with spatulate shaped tepals.
Figure 3:
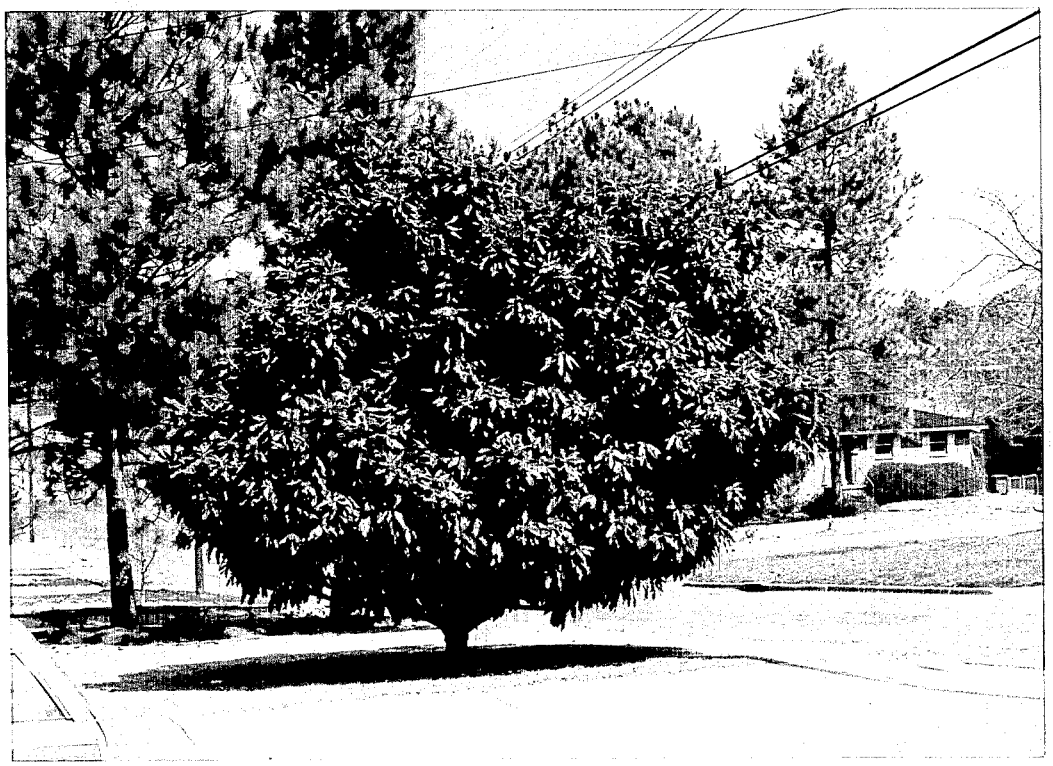
FIG. 3 exhibits overall growth habit of a tree 15 years old.

Below is a detailed description of the new selection, all color terminology is derived from The British Horticultural Colour Charts:

Overall size: After 16 years of growth, tree is 16 feet tall and 25 feet wide. Growth habit appears to broaden with age.

Growth rate: Rapid to medium growth dependent upon feeding. Under ideal growth conditions, this selection will grow 2 feet per year.

Cold hardiness: USDA Zone 6 to −10° F. Tolerates 10° F. less than *Magnolia grandiflora.*

Inflorescence:

*Size.*—9 to 10 inches in diameter.

*Tepals.*—Texture: heavy, thick. Color: creamy white. Number: varies from 9 to 12. Shape: spatulate. Length: ranges from 2½" to 4½". Width: ranges from 1½" to 3". Fragrance: sweet heavy scent.

*Foliage.*—Persistence: evergreen. Shape: elliptic to obovate-elliptic. Leaf Tip: acute. Leaf Base: narrowly attenuate. Margins: entire, strongly undulate, particularly on mature foliage. Width: ranges 2½"–4½" with average of 3¾ inches. Texture: coriaceous. Length: ranges 6–9¾" with average of 8¾ inches. Average length/width ratio: 2.26/1. Color: mature upper leaf: spinach green 0960. juvenile upper leaf: fern green 0862. Arrangement: alternate. Petiole length: varies in length ⅞" to 1¼" pubescent. Hair covering: upper leaf surface: smooth, shiny, glabrous. lower leaf surface: pubescent, short brown hairs densely prevalent on juvenile foliage, sparse on mature foliage. Petiole: densely tomentose.

Fruit: production of fruit cones is extremely rare, ranging from none to 4 per year.

*Cone length.*—1½–2" long, irregular shaped.

Seed: per fruit cone number averages 1 or 2 seed, the maximum number was a dozen seed. Seed is sterile as it has never germinated over the past 3 years.

I claim:

1. A new and distinct selection of Magnolia as substantially shown and described herein, characterized particularly as to novelty by the unique combination of continuously heavy blooming due to a unique blooming pattern, longer foliage which forms a dense crown, a growth habit which is wide spreading and few to no fruit cones produced.

* * * * *